(12) United States Patent
Marynen et al.

(10) Patent No.: US 8,173,423 B2
(45) Date of Patent: May 8, 2012

(54) DIAGNOSIS AND TREATMENT OF T-CELL ACUTE LYMPHOBLASTIC LEUKEMIA

(75) Inventors: Peter Marynen, Herent (BE); Jan Cools, Herent (BE); Idoya Lahortiga, Leuven (BE)

(73) Assignees: VIB VZW, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 1 day.

(21) Appl. No.: 12/312,355

(22) PCT Filed: Nov. 7, 2007

(86) PCT No.: PCT/EP2007/061988
§ 371 (c)(1),
(2), (4) Date: Jan. 27, 2010

(87) PCT Pub. No.: WO2008/055924
PCT Pub. Date: May 15, 2008

(65) Prior Publication Data
US 2010/0130586 A1 May 27, 2010

Related U.S. Application Data

(60) Provisional application No. 60/857,302, filed on Nov. 7, 2006.

(51) Int. Cl.
*C12N 15/85* (2006.01)
*C12Q 15/63* (2006.01)
*C07H 21/02* (2006.01)
*C07H 21/04* (2006.01)

(52) U.S. Cl. ............ 435/325; 435/6; 536/23.1; 536/24.5

(58) Field of Classification Search ........................ None
See application file for complete search history.

(56) References Cited

U.S. PATENT DOCUMENTS
2006/0205666 A1  9/2006  Mori

FOREIGN PATENT DOCUMENTS

| WO | WO 94/01131 | 1/1994 |
|---|---|---|
| WO | WO 94/04678 | 3/1994 |
| WO | WO 94/25591 | 10/1994 |
| WO | WO 97/49805 | 12/1997 |
| WO | WO 99/14220 | 3/1999 |
| WO | WO 03/013527 | 2/2003 |
| WO | WO 03/070917 A | 8/2003 |
| WO | WO 2008/055924 A1 | 5/2008 |

OTHER PUBLICATIONS

Sinclair et al. (haematolgica/the hematology journal, 90(5), 2005, pp. 602-611).*
Mavilio et al. (Proc. Natl. Acad. Sci., vol. 83, pp. 4394-4398, 1986).*
Bertrand et al. (Biochemical and Biophysical Research Communications, 296, 2002, pp. 1000-1004).*
Liu et al. (The Journal of Neuroscience, 2004, 24(40), pp. 8720-8725).*
Miele et al. (Clin Cancer Res, 2006, 12, pp. 1074-1079).*
Barletta et al., Relationship Between the c-myb Locus and the 6q-Chromosomal Aberration in Leukemias and Lymphomas, Science, Dec. 1986, pp. 1064-1067, vol. 235.
Calabretta et al., Normal and leukemic hematopoietic cells manifest differential sensitivity to inhibitory effects of c-myb antisense oligodeoxynucleotides: An in vitro study relevant to bone marrow purging, Proc. Natl. Acad. Sci., Mar. 1991, pp. 2351-2355, vol. 88.
Clappier et al., The C-MYB locus is involved in chromosomal translocation and genomic duplications in human T-cell acute leukemia (T-ALL), the translocation defining a new T-ALL subtype in very young children, Blood, 2007, pp. 1251-1261, vol. 110.
Hess et al., c-Myb is an essential downstream target for homeobox-mediated transformation of hematopoietic cells, Blood, 2006, pp. 297-304, vol. 108.
Lahortiga et al., Duplication of the MYB oncogene in T cell acute lymphoblastic leukemia, Nature Genetics, May 2007, pp. 593-595, vol. 39, No. 5.
O'Neil et al., Mechanisms of transcription factor deregulation in lymphoid cell transformation, Oncogene, 2007, pp. 6838-6849, vol. 26.
Pelicci et al., Amplification of the c-myb Oncogene in a Case of Human Acute Myelogeous Leukemia, Science, Jun. 8, 1984, pp. 1117-1121, vol. 224.
Ratajczak et al., In vivo treatment of human leukemia in a scid mouse model with c-myb antisense oligodeoxynucleotides, Proc. Natl. Acad. Sci., Dec. 1992, pp. 11823-11827, vol. 89.
Wang et al., Activating Mutations of NOTCH1 in Human T Cell Acute Lymphoblastic Leukemia; Science, Oct. 8, 2004, pp. 269-271, vol. 306, with supporting online material.
Barletta et al., Relationship between the c-myb locus and the 6q-chromosomal aberration in leukemias and lymphomas, Science, Feb. 27, 1987, pp. 1064-1067, vol. 235, No. 4792.
Pelicci et al., Amplification of the c-myb oncogene in a case of human acute myelogenous leukemia, Science, Jun. 8, 1984, pp. 1117-1121, vol. 224, No. 4653.
Hess et al., c-Myb is an essential downstream target for homeobox-mediated transformation of hematopoietic cells, Blood, Jul. 2006, pp. 297-304, vol. 108, No. 1.
Clappier et al., The C-MYB locus is involved in chromosomal translocation and genomic duplications in human T-cell acute leukemia (T-ALL), the translocation defining a new T-ALL subtype in very young children, Blood, Aug. 2007, pp. 1251-1261, vol. 110, No. 4.
O'Neil et al., Mechanisms of transcription factor deregulation in lymphoid cell transformation, Oncogene, Oct. 2007, pp. 6838-6849, vol. 26, No. 47.
Lahortiga et al., Duplication of the MYB oncogene in T cell acute lymphoblastic leukemia, Nature Genetics, May 2007, pp. 593-595, vol. 39, No. 5.
PCT International Search Report, PCT/EP2007/061988, dated Feb. 26, 2008.

* cited by examiner

*Primary Examiner* — Amy Bowman
(74) *Attorney, Agent, or Firm* — TraskBritt

(57) ABSTRACT

The present invention relates to the field of biotechnological means to diagnose or treat T-cell acute lymphoblastic leukaemia. More particularly, the invention relates to methods to diagnose T-cell acute lymphoblastic leukaemia via determining the presence of a duplication of the MYB gene in cells taken from patients. The invention further relates to inhibitors capable of neutralizing the biological activity of MYB alone, or in combination with inhibitors capable of neutralizing the biological activity of NOTCH1, which can be used to treat T-cell acute lymphoblastic leukaemia.

12 Claims, 1 Drawing Sheet

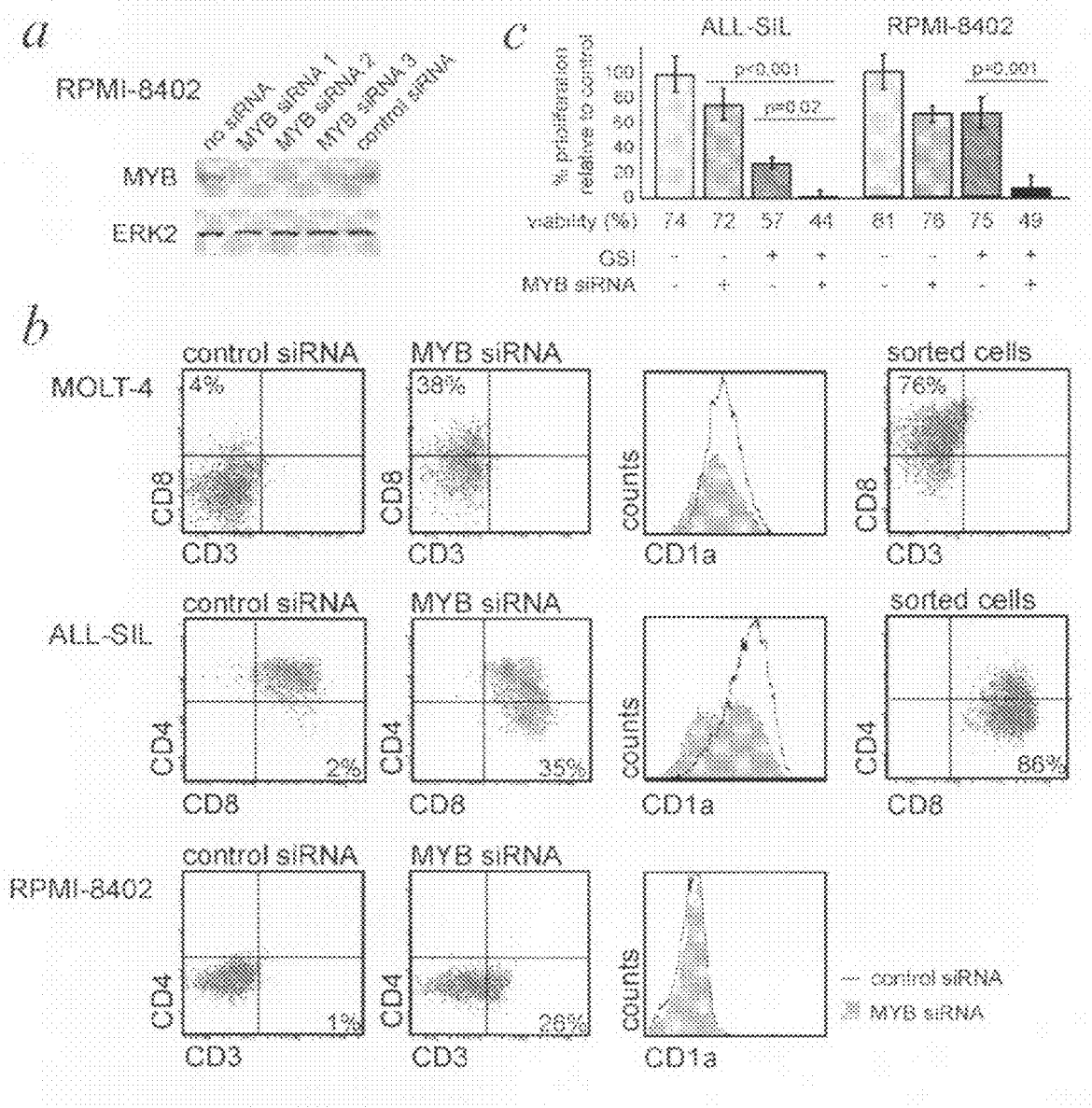

```
SEQUENCE LISTING

<160> NUMBER OF SEQ ID NOS: 8

<210> SEQ ID NO 1
<211> LENGTH: 25
<212> TYPE: RNA
<213> ORGANISM: Artificial
<220> FEATURE:
<223> OTHER INFORMATION: MYB siRNA sequence

<400> SEQUENCE: 1
uauagugucu cugaauggcu gcggc                                            25

<210> SEQ ID NO 2
<211> LENGTH: 25
<212> TYPE: RNA
<213> ORGANISM: Artificial
<220> FEATURE:
<223> OTHER INFORMATION: Complementary strand MYB siRNA

<400> SEQUENCE: 2
gccgcagcca uucagagaca cuaua                                            25

<210> SEQ ID NO 3
<211> LENGTH: 20
<212> TYPE: DNA
<213> ORGANISM: Artificial
<220> FEATURE:
<223> OTHER INFORMATION: ABL1-F primer

<400> SEQUENCE: 3
ggtgtgaagc ccaaaccaaa                                                  20

<210> SEQ ID NO 4
<211> LENGTH: 22
<212> TYPE: DNA
<213> ORGANISM: Artificial
<220> FEATURE:
<223> OTHER INFORMATION: ABL1-R primer

<400> SEQUENCE: 4
tgactggcgt gatgtagttg ct                                               22

<210> SEQ ID NO 5
<211> LENGTH: 21
<212> TYPE: DNA
<213> ORGANISM: Artificial
<220> FEATURE:
```

```
<223> OTHER INFORMATION: TIE1-F primer

<400> SEQUENCE: 5
cgagatccag ctgacatgga a                                         21

<210> SEQ ID NO 6
<211> LENGTH: 24
<212> TYPE: DNA
<213> ORGANISM: Artificial
<220> FEATURE:
<223> OTHER INFORMATION: TIE1-R primer

<400> SEQUENCE: 6
ctccacaacg tacttggata ttgg                                      24

<210> SEQ ID NO 7
<211> LENGTH: 23
<212> TYPE: DNA
<213> ORGANISM: Artificial
<220> FEATURE:
<223> OTHER INFORMATION: MYB-F primer

<400> SEQUENCE: 7
gaacaccact ccactccatc tct                                       23

<210> SEQ ID NO 8
<211> LENGTH: 17
<212> TYPE: DNA
<213> ORGANISM: Artificial
<220> FEATURE:
<223> OTHER INFORMATION: MYB-R primer

<400> SEQUENCE: 8
ggcgaggcgc tttcttc                                              17
```

DIAGNOSIS AND TREATMENT OF T-CELL ACUTE LYMPHOBLASTIC LEUKEMIA

TECHNICAL FIELD

The present invention relates to the field of biotechnological means to diagnose or treat T-cell acute lymphoblastic leukaemia. More particularly, the invention relates to methods to diagnose T-cell acute lymphoblastic leukaemia via determining the presence of a duplication of the MYB gene in cells taken from patients. The invention further relates to inhibitors capable of neutralizing the biological activity of MYB alone, or in combination with inhibitors capable of neutralizing the biological activity of NOTCH1, which can be used to treat T-cell acute lymphoblastic leukaemia.

BACKGROUND

T-cell acute lymphoblastic leukemia (T-ALL) is an aggressive T-cell malignancy that is most common in children and adolescents.

Leukemic transformation of thymocytes is caused by the cooperation of mutations that affect proliferation, survival, cell-cycle, and T-cell differentiation. Molecular analyses have identified a large number of T-ALL specific genetic alterations including deletion of CDKN2A (p16), ectopic expression of transcription factors, episomal amplification of ABL1, and mutation of NOTCH1.[1-4]

Inhibition of NOTCH1 activation by treatment with a gamma-secretase inhibitor (GSI) was shown to inhibit the proliferation of the T-ALL cell lines ALL-SIL and RPMI-8402.[4] The MYB gene encodes a nuclear transcription factor that is implicated in proliferation, survival and differentiation of hematopoietic progenitor cells.[10] Proper levels of MYB expression were shown to be important during several steps of hematopoietic cell development, and overexpression of MYB impairs hematopoietic differentiation.[11, 12] A viral form of the MYB gene is present in the avian myeloblastosis and E26 viruses, and the Myb gene is a frequent target of retroviral insertions in myeloid, B- and also T-cell leukemias.[8, 13, 14] To date, however, no abnormalities affecting MYB have been identified in human T-ALL and it has not been documented that inhibitors of MYB alone, or in combination with inhibitors of NOTCH1, affect differentiation, proliferation and/or survival of T-ALL cells.

BRIEF DESCRIPTION OF THE FIGURES

FIG. 1: Effect of knockdown of MYB expression on T-ALL cell lines. (a) Protein blot analysis showing that electroporation of three different MYB siRNAs in RPMI-8402 cells causes a decrease of MYB expression, compared with electroporation with no siRNA or control siRNA (ERBB4). (b) Knockdown of MYB using MYB siRNA 1 results in the differentiation of the ALL-SIL, RPMI-8402 and MOLT-4 cell lines, as observed by changes in expression of CD1a, CD3, CD4 or CD8 cell surface markers. Differentiated cells were separated from undifferentiated cells by flow sorting, and analysis of the sorted cells 10 d later indicates that the differentiation is irreversible. (c) Treatment of ALL-SIL and RPMI-8402 cells with gamma-secretase inhibitor (GSI), MYB siRNA or a combination of both treatments indicates that knockdown of MYB expression in combination with GSI treatment blocks cell proliferation and affects cell survival. Control cells were treated with dimethylsulfoxide or a control siRNA. Error bars indicate s.e.m.

DETAILED DESCRIPTION OF THE INVENTION

In the present invention, it is shown that the MYB gene is frequently duplicated in T-ALL patients. Also evidence is provided that: 1) duplication of MYB interferes with normal differentiation of T cells, and 2) MYB cooperates with NOTCH1 in the development of T-ALL. While interference with MYB function mainly affects differentiation, a combined inhibition of MYB and NOTCH1 strongly affects proliferation and survival of T-ALL cells establishing MYB as a novel target for therapy in T-ALL.

A first aspect of the invention concerns a method of diagnosing T-cell acute lymphoblastic leukaemia in a subject, said method comprising determining the presence of a duplication of the MYB gene in a sample of said subject. With the feature 'a sample of said subject' is meant any possible part or portion taken from the body of a T-ALL patient which contains T cells such as blood, bone marrow, lymph, a biopsy of a lymph node, of the spleen and the like. Once such a sample is taken from the patient, any standard method to extract DNA or RNA from said sample—as for example described in Genome Analysis, A laboratory Manual, eds E.D. Green et al. Cold Spring Harbor Laboratory Press, 1997—can be used. It is further clear that any methodology known to the skilled person allowing him to demonstrate the presence of said MYB gene, or a duplication of said MYB gene containing at least 3 copies of said MYB gene, such as hybridization, (quantitative) polymerase chain reaction, FISH and the like can be used. Another aspect of the invention regards a method to modulate T-cell differentiation comprising administering a MYB specific inhibitor. Indeed, the present invention discloses that downregulation of MYB via a MYB inhibitor such as a MYB specific siRNA affected the differentiation of the T-cells without affecting the cell cycle of said cells. A skilled person will comprehend that any type of inhibitor which is capable of neutralizing the biological activity of MYB can be used. A list of non-limiting examples include ribozymes, siRNA's, antisense nucleic acids, locked nucleic acids (LNA's) as described in WO99/14220, peptides, small organic molecules, antibodies such as camel antibodies as described in WO94/25591, WO94/04678 and in WO97/49805. Since MYB is an intracellular target, the antibodies or functional fragments thereof must be delivered into the T cell. One such methodology uses lipidation of antibodies as described in WO94/01131.

LNA-modified oligonucleotides based on the MYB sequence can be used for the treatment of T-ALL. In general, therapeutic methods of the invention for the treatment of T-ALL include administration of a therapeutically effective amount of an LNA-modifies oligonucleotide to a mammal, particularly a human. In antisense therapies, administering LNA-modified oligonucleotide interacts with the targeted MYB mRNA whereby expression of MYB is inhibited and differentiation of the T cell modulated. Such inhibition of MYB expression suitably will be at least a 10% or 20% difference relative to a control, more preferably at least 30%, 40%, 50%, 60%, 70%, 80% or 90% difference in expression relative to a control.

Hence, it is clear that the present invention relates to inhibitors capable of neutralizing the biological activity of MYB that can be used for the manufacturing of a medicament to treat T-ALL. The term 'medicament' relates to a composition comprising molecules as described above and a pharmaceutically acceptable carrier or excipient. Suitable carriers or excipients and suitable methods and routes of administration are known to the skilled person. However, the dosage and mode of administration will depend on the individual. Generally, the medicament is administered so that the inhibitor of the present invention is given at a dose between 1 μg/kg and 10 mg/kg. Another aspect of administration for treatment is the use of gene therapy to deliver the above mentioned anti-sense gene of the MYB gene or a part thereof, or, a ribozyme directed against the MYB mRNA or a part thereof. Gene therapy is—for example—extensively reviewed in Lever and Goodfellow 1995; Br Med Bull 51, 1-242.

Another aspect of the invention regards a method to inhibit proliferation and induce cell death of T-ALL cells by administering a MYB specific inhibitor in combination with a NOTCH1 inhibitor (or gamma-secretase inhibitor that also inhibits the activation of NOTCH1). Indeed, the present invention discloses that downregulation of MYB via a MYB inhibitor such as a MYB specific siRNA in combination with treatment with a gamma-secretase small molecule inhibitor affected the proliferation of the T-cells and induced cell death of said cells. Surprisingly, the present invention discloses that downregulation of MYB expression in combination with inhibition of the biological activity of NOTCH1 resulted in a strong synergistic effect on proliferation and viability of the latter T-cells. With the term 'synergism' is meant that the combined inhibition of the biological activity of both MYB and NOTCH1 is greater than the sum of the effects of the inhibition of the biological activity of MYB and NOTCH1 separately. Similar as described above for a MYB specific inhibitors, it is clear to a person skilled in the art that any type of NOTCH1 inhibitor capable of decreasing or inhibiting—relative to a control—the biological activity of NOTCH1 can be used. Selective NOTCH1 inhibitors include anti-sense nucleic acids, monoclonal antibodies, and RNA interference nucleic acids. Antibodies against a Notch ligand such as DLL4 (J Natl Cancer Inst 2007; 99: 991-5) can also be used. Nonselective inhibitors of NOTCH1 include soluble or cell-associated Notch decoys, γ-secretase inhibitors, intracellular MAML1 decoys, and Ras signaling inhibitors. γ-Secretase inhibitors (GSI) have the most immediate therapeutic potential. GSI cbz-IL-CHO has Notch-1—dependent antineoplastic activity in Ras-transformed fibroblasts (Miele L. Clinical Cancer Research Vol. 12, 1074-1079, February 2006). GSI z-Leu-leu-Nle-CHO induces apoptosis in melanoma cell lines and melanoma xenografts, but not normal melanocytes, via p53-independent up-regulation of NOXA (Miele L. Clinical Cancer Research Vol. 12, 1074-1079, February 2006). GSI compound E ((S, S)-2-[2-(3,5-Difluorophenyl)-acetylamino]-N-(1-methyl-2-oxo-5-phenyl-2,3-dihydro-1H-benzo[e][1,4]diazepin-3-yl)-propionamide) causes growth arrest in T-ALL cells (Miele L. Clinical Cancer Research Vol. 12, 1074-1079, February 2006). Blocking specific E3 ligases responsible for ubiquitination of Notch ligands or mono-ubiquitination of Notch receptors can also be used. Still other NOTCH1 inhibitors that can be used are described in WO 2003/013527 and paragraphs 0016-0019 of US 2006/205666

The present invention further relates to a method to screen for compounds capable of inducing an irreversible differentiation of T-cell acute lymphoblastic leukaemia cells or capable of decreasing proliferation and/or survival of T-cell acute lymphoblastic leukaemia cells comprising: 1) exposing nucleic acids encoding for MYB or the MYB nuclear transcription factor encoded by said nucleic acids to at least 1 compound; and 2) determining if said compound induces an irreversible differentiation of T-cell acute lymphoblastic leukaemia cells or, when administered in combination with a NOTCH1 specific inhibitor, decreases or blocks proliferation and/or survival of T-cell acute lymphoblastic leukaemia cells. The latter 'compound' can be any kind of molecule capable of inducing an irreversible differentiation of T-cell acute lymphoblastic leukaemia cells or capable of decreasing proliferation and/or survival of T-cell acute lymphoblastic leukaemia cells including ribozymes, siRNA's, anti-sense nucleic acids, locked nucleic acids (LNA's) as described in WO99/14220, peptides, small organic molecules or antibodies such as camel antibodies as described above. Determining if said compound induces an irreversible differentiation of T-cell acute lymphoblastic leukaemia cells or, when administered in combination with a NOTCH1 specific inhibitor, decreases or blocks proliferation and/or survival of T-cell acute lymphoblastic leukaemia cells can be for example performed as described further in the example section or in any other way known to the skilled person.

EXAMPLES

In order to detect novel unbalanced genomic rearrangements in T-ALL, we have performed array comparative genomic hybridization (array CGH),[5] using an array with genomic BAC and PAC probes with an overall resolution of 1 Mb over the entire genome, but with additional probes around known oncogenes and candidate oncogenes such as the 90 protein tyrosine kinase genes.

An initial screening of 27 T-ALL samples revealed an increased copy number of a small region (<2 Mb) at chromosome 6q23 in 2 individuals. The copy number change was detected with 2 probes covering the MYB locus, and flanking probes on the array were unaffected. Quantitative PCR (Q-PCR) revealed that this copy number change was a duplication of MYB, that was present in these 2 individuals and was absent in the 25 other individuals with T-ALL. In addition, Q-PCR analysis of DNA samples from diagnosis and remission showed the presence of the duplication in samples from diagnosis only, confirming that the duplication was an acquired event. The flanking genes HBS1L and AHI1 were not duplicated in these 2 individuals, limiting the duplication exclusively to MYB (Table 1).

TABLE 1

Copy number of MYB and flanking genes in individuals and cell lines with MYB duplication.

| | Copy number as determined by quantitative PCR | | | | |
|---|---|---|---|---|---|
| | SGK | HBS1L | MYB | AHI1 | BCLAF1 |
| Individual | | | | | |
| 1 | 2 | 2 | 3* | 2 | 2 |
| 2 | 2 | 2 | 3* | 2 | 2 |
| 3 | 2 | 2 | 3 | 2 | 2 |
| 4 | 3 | 3 | 3 | 3 | 2 |
| 5 | 2 | 2 | 3 | 2 | 2 |
| 6 | 4 | 4 | 4 | 4 | 2 |
| 7 | 2 | 3 | 3 | 3 | 2 |
| 8 | 3 | nd | 3 | nd | 2 |
| 9 | 2 | 2 | 3* | 2 | 2 |
| 10 | 2 | 2 | 3 | 2 | 2 |
| 11 | nd | nd | 3 | nd | nd |

TABLE 1-continued

Copy number of MYB and flanking genes in individuals and cell lines with MYB duplication.

| | Copy number as determined by quantitative PCR | | | | |
|---|---|---|---|---|---|
| | SGK | HBS1L | MYB | AHI1 | BCLAF1 |
| Cell line | | | | | |
| ALL-SIL | normal | dup | dup | dup | dup |
| RPMI-8402 | normal | dup | dup | dup | normal |
| MOLT-4 | normal | normal | dup | normal | normal |
| P12-ICHIKAWA | normal | dup | dup | dup | dup |
| CCRF-CEM | dup | dup | dup | dup | normal | nd, not determined;
dup, duplicated.
Note:
The cell lines have an increased number of chromosomes per cell, which is not completely stable. As a consequence, it is difficult to provide the exact copy number of the genes. We determined whether the copy number was normal (similar to 2 control genes ABL1 and TIE1) or duplicated (increased copy number compared to ABL1 and TIE1).
*The duplication in these individuals was confirmed to be an acquired duplication by analysis of DNA extracted from bone marrow cells at time of remission.

Fluorescence in situ hybridization (FISH) revealed that the duplication of MYB was a local duplication with the extra copy of the MYB gene located at chromosome 6q23.

We next screened an independent set of 107 individuals with T-ALL and 12 T-ALL cell lines by Q-PCR. Duplication of MYB was detected in 9 of 107 (8.4%) individuals and in 5 cell lines (ALL-SIL, MOLT-4, P12-ICHIKAWA, CCRF-CEM and RPMI-8402). The flanking genes HBS1L and AHI1 were duplicated in some patients, but the commonly duplicated region only covered the MYB gene (Table 1). Fluorescence in situ hybridization (FISH) revealed that the duplication of MYB was a local duplication with the extra copy of MYB located at chromosome 6q. Although the expression level of MYB was highly variable in T-ALL, likely to reflect the stage of T-cell differentiation,[9] the mean expression level of MYB was found to be significantly elevated (3 fold) in T-ALL cases with MYB duplication compared to the other cases. In T-ALL cell lines, MYB expression was also variable, with MOLT-4 and RPMI-8402 (both with MYB duplication) showing high level MYB expression.

The MYB gene encodes a nuclear transcription factor that is implicated in proliferation, survival and differentiation of hematopoietic progenitor cells.[10] Proper levels of MYB expression are important during hematopoietic cell development, and overexpression of MYB is implicated in murine leukemogenesis.[9, 11-14] To determine a role for MYB duplication in the pathogenesis of human T-ALL, we downregulated MYB expression in T-ALL cell lines (FIG. 1a). Knockdown of MYB expression resulted in an irreversible differentiation of RPMI-8402, MOLT-4 and ALL-SIL cells, but not of cell lines without MYB duplication, as reported by changes in expression of the CD1a, CD3, CD4 or CD8 markers (FIG. 1b).

Downregulation of MYB expression had only a limited effect on the viability, proliferation and cell cycle (FIG. 1c). Since NOTCH1 was recently identified as a possible therapeutic target in T-ALL,[4] and since 7 of 10 T-ALL cases and all 5 T-ALL cell lines with MYB duplication also harbored mutation of NOTCH1 (Table 2), we tested the effect of inhibition of NOTCH1 combined with MYB siRNA treatment. As previously shown, inhibition of NOTCH1 activation by treatment with a gamma-secretase inhibitor (GSI) led to inhibition of the proliferation of ALL-SIL and RPMI-8402.[4] Downregulation of MYB expression in combination with GSI treatment resulted in a strong syntergistic effect on proliferation and viability (FIG. 1c). MOLT-4 is not sensitive to GSI treatment and could not be used for this analysis.[4] Thus, while interference with MYB function mainly affects differentiation, a combined inhibition of MYB and NOTCH1 strongly affects proliferation and survival, establishing MYB as a novel target for therapy in T-ALL.

TABLE 2

Cytogenetic and molecular characteristics of individuals with T-ALL with MYB duplication.

| Ind | karyotype | NOTCH1 mutation | CDKN2A | Other* |
|---|---|---|---|---|
| 1 | 46, XY[10] | Del P1583 Q2459*(stop) | +/+ | ND |
| 2 | 46, XY, del(9)(p13) [5] | F1593S | +/− | NA |
| 3 | 46, XX, del(14)(q21q31)[4] | ND | +/+ | ND |
| 4 | NA | InsS2468SRCHPRYSHP*(stop) | +/+ | ND |
| 5 | 46, XX[30] | NA | −/− | ND |
| 6 | NA | Del/InsFKRDA1607-1611PSDLRLGGSDT | +/− | ND |
| 7 | 46, XY, t(11, 14)(p15, q11)[3] | Del/InsFK1607-1608RSE | −/− | LMO1+ TAL2+ |
| 8 | NA | ND | +/− | ND |
| 9 | 46, XY, t(10; 14)(q2?4; q11)[2]/ 46, idem, del(12)(p11)[10]/ 46, idem, t(6; 7)(p21; q34~35), del(12)(p11)[3]/46, XY[9] | V1605G | −/− | TLX1+ |
| 10 | 46, XY, del(6)(q15q21), del(14)(q11q32), der(14)inv(14)/ 46, idem, dup(1)?(q21q42)[2]/46, idem, del(17)(p11)[4] | L1679P | +/+ | ND |
| 11 | NA | ND, (V2286I, SNP) | +/+ | ND |

Ind, individual;
NA, not available;
ND, none detected.
*Chromosomal rearrangements and expression of LMO1, TAL1, SIL-TAL, TLX1, and TLX3 was investigated.
Duplication of MYB was not associated with various clinical parameters, such as age, gender, white blood cell count and relapse rate.

Methods

Affected Individuals.

We retrospectively selected 27 individuals with T-ALL from the database of the Department of Human Genetics (Leuven) for the initial array-CGH screening. We later screened a set of 107 individuals with T-ALL from the Erasmus Medical Center/Sophia Children's Hospital (Rotterdam) for the presence of the MYB duplication by Q-PCR. We reviewed the clinical diagnosis, morphology and immunophenotypic data. This study was approved by the Ethical Committee of the Medical Faculty of the University of Leuven and informed consent was obtained from all subjects.

Cytogenetics and FISH.

We carried out cytogenetic studies on bone marrow or blood cells using direct or short-term cultures without mitogens and R banding. We carried out FISH on stored fixed cell suspension originally used for karyotyping, as described. On average, we scored ten metaphases and 200 nuclei. We obtained BAC probes from the RPCI11 library.

Array CGH.

We carried out array CGH using Code Linked Slides (AP Biotech) containing the 3,527 BAC clones from the Wellcome Trust Sanger Institute 1 Mb Clone Set, a gift from N. P. Carter (The Wellcome Trust Sanger Institute, UK). Additional clones covering all 90 protein tyrosine kinase genes were added to this set. Clones that are present on the array slides are referred to as 'probes' in the text. The array CGH data are available at Gene Expression Omnibus (http://www.ncbi.nlm.nih.gov/geo).

Cell Culture

DND-41, HSB-2, RPMI-8402, ALL-SIL, MOLT-4, LOUCY, P12-ICHIKAWA, CCRF-CEM (DSMZ, Braunschweig, Germany) were cultured in RPMI-1640 supplemented with 20% fetal calf serum. The number or percentage of viable cells was counted with a Vi-cell XR cell viability analyzer (Beckman Coulter, Fullerton, Calif.). For differentiation experiments, cells were cultured during a period of 6 days and electroporated on the first day and again on the 4th day with 50 nM siRNA. MYB stealth select siRNAs were purchased from Invitrogen (Carlsbad, Calif.). MYB siRNA1 (MYB-HSS106819, sequence:5'UAUAGUGUCU-CUGAAUGGCUGCGGC SEQ ID NO:1) was found to be the most efficient siRNA and was used in the differentiation experiments. Electroporation with a stealth siRNA directed against ERBB4 (Invitrogen, Carlsbad, Calif.), a gene not expressed in these cell lines, served as a control. FACS analysis with a FITC labeled siRNA (Invitrogen) indicated that transfection efficiencies were generally >55%. For inhibition of NOTCH1, we treated the cell ines with 1 µM of Compound E (gamma-secretase inhibitor XXI, Calbiochem, San Diego, Calif.) or DMSO (control). The percentage proliferation was calculated by comparing the increase of the number of viable cells from treated cells to the increase of the number of viable cells treated with DMSO and electroporated with a control siRNA, and this for a proliferation period of 3 days.

FACS Analysis.

Analysis of CD1a, CD3, CD4 and CD8 expression and cell cycle analysis was performed on $0.3\text{-}1\times10^6$ cells 6 days after the first electroporation with siRNA. We used the PE/CD1a, and the TriTEST CD4 FITC/CD8 PE/CD3 PerCP Reagent kit (Becton Dickinson, San Jose, Calif.) and the CycleTEST™ PLUS DNA Reagent Kit (Becton Dickinson). After staining, the cells were detected on a FACSCanto Flow Cytometer (Becton Dickinson) and the data were analyzed with the BD FACSDiva software (Becton Dickinson). Unstained cells and cells treated with ERBB4 siRNA were used as controls. Cell sorting was performed after staining of the cells with the TriTEST CD4/CD8/CD3 kit. Cells were separated into two fractions (differentiated and undifferentiated) using the FACSVantage SE system (Becton Dickinson).

siRNA Knock Down of MYB.

Cell lines were electroporated every four days with 50-250 nM siRNA. MYB stealth select siRNAs (MYB-HSS106819) were purchased from Invitrogen (Carlsbad, Calif.). Control samples were electroporated with a random siRNA, subsequent FACS analysis indicated that transfection efficiencies were generally >55%.

```
(MYB siRNA sequence:
5' UAUAGUGUCUCUGAAUGGCUGCGGC 3',    (SEQ ID NO: 1)

with complementary strand:
5' GCCGCAGCCAUUCAGAGACACUAUA 3').   (SEQ ID NO: 2)
```

Real-Time Quantitation of DNA Copy Number.

We used the comparative ddCt method (Sequence Detection System bulletin 2 [Applied Biosystems]) with SYBR-green for confirmation of our array-CGH data. Primers were designed with PrimerExpress software (Applied Biosystems) and are shown below. We first validated whether the efficiency of amplification of the chosen primer sets was equal to that of the normalizer. A primer set for the ABL1 and TIE1 genes was used for normalization. The validation experiments were performed on fourfold dilutions of genomic DNA, starting with 100 ng in the first dilution. For relative quantitation, the reaction mixtures consisted of qPCR Mastermix Plus for SYBR Green I (Eurogentec), (LightCycler 480 SYBR Green I Master (Roche)) with 500 nM of each primer and 10 ng DNA in a total volume of 25 µl. After an initial denaturation step for 10 min at 95° C., thermal cycling conditions were 15 s at 95° C. and 1 min at 60° C. for 40 cycles. Finally, the dissociation curves for each reaction were determined. All samples were run in duplicate on an ABI PRISM 7000 instrument (LightCycler 480 Instrument (Roche)).

The expression level of MYB transcripts was quantified relative to the expression level of the gene glyceraldehyde-3-phosphate dehydrogenase (GAPDH) by real-time PCR using an ABI 7700 sequence detection system (PE Applied Biosystems, Fostercity Calif., USA), as described previously.[15] The expression levels relative to the GAPDH housekeeping gene were calculated following the equation: Relative expression level as percentage of GAPDH expression=$2^{-\Delta Ct}\times100\%$, where $\Delta Ct=Ct_{target}-Ct_{GAPDH}$.

Primers Used:

```
ABL1-F
5'/GGTGTGAAGCCCAAACCAAA         (SEQ ID NO: 3)

ABL1-R
5'/TGACTGGCGTGATGTAGTTGCT       (SEQ ID NO: 4)

TIE1-F
5'/CGAGATCCAGCTGACATGGAA        (SEQ ID NO: 5)

TIE1-R
5'/CTCCACAACGTACTTGGATATTGG     (SEQ ID NO: 6)

MYB-F
5'/GAACACCACTCCACTCCATCTCT      (SEQ ID NO: 7)

MYB-R
5'/GGCGAGGCGCTTTCTTC            (SEQ ID NO: 8)
```

Statistical Analysis.

The difference in MYB expression between T-ALL cases with MYB duplication and cases without MYB duplication was calculated with a Mann-Whitney-U test. Association between MYB duplication and age or white blood cell count was calculated with a Mann-Whitney-U test, while association between MYB duplication and sex or relapse rate was calculated with a chi-square test. A one way ANOVA test was used to determine significant differences between different treatments of the cell lines.

URLs.

Locations of genes and probes, and gene structures were determined based on Ensembl data available on the world wide web at ensemble.org. Genomic alterations that involve segments of DNA that are larger than >1 kb and are found in the general population are collected in the Database of Genomic Variants available on the world wide web at tcag.ca/variation.[7,8] Retroviral insertion sites can be viewed using the Mouse Retrovirus Tagged Cancer Gene Database available on the world wide web at rtcgd.ncifcrf.gov.[16]

REFERENCES

1. Pui, C. H. et al. *N. Engl. J. Med.* 350, 1535-1548 (2004).
2. Grabher, C. et al. *Nat. Rev. Cancer* 6, 347-359 (2006).
3. De Keersmaecker, K. et al. *Haematologica* 90, 1116-1127 (2005).
4. Weng, A. P. et al. *Science* 306, 269-271 (2004).
5. Graux, C. et al. *Nat. Genet.* 36, 1084-1089 (2004).
6. Speicher, M. R. & Carter, N. P. *Nat. Rev. Genet.* 6, 782-792 (2005).
7. Iafrate, A. J. et al. *Nat. Genet.* 36, 949-951 (2004).
8. Redon, R. et al. *Nature* 444, 444-454 (2006).
9. Bender, T. P. et al. *Nat. Immunol.* 5, 721-729 (2004).
10. Rothenberg, E. V. & Taghon, T. *Annu. Rev. Immunol.* 23, 601-649 (2005).
11. Hess, J. L. et al. *Blood* 108, 297-304 (2006).
12. Sakamoto, H. et al. *Blood* 108, 896-903 (2006).
13. Lund, A. H. et al. *Nat. Genet.* 32, 160-165 (2002).
14. Suzuki, T. et al. *Nat. Genet.* 32, 166-174 (2002).
15. Meijerink J., et al. *J. Mol. Diagn.* 3, 55-61 (2001).
16. Akagi, K. et al. *Nucleic Acids Res.* 32, D523-D527 (2004).

The invention claimed is:

1. A method to decrease proliferation and/or survival of T-cell acute lymphoblastic leukemia cell, said method comprising
   determining the presence of a duplication of the MYB gene in the T-cell acute lymphoblastic leukemia cell; and
   administering to the T-cell acute lymphoblastic leukemia cells an MYB specific inhibitor able to neutralize the biological activity of MYB.

2. The method according to claim 1, wherein the presence of a duplication of the MYB gene is determined by an assay comprising a quantitative polymerase chain reaction.

3. The method according to claim 1, wherein the MYB specific inhibitor is a MYB specific siRNA.

4. The method according to claim 1, further comprising administering a NOTCH1 specific inhibitor.

5. The method of claim 4, wherein said MYB specific inhibitor is a MYB specific siRNA and wherein said NOTCH1 specific inhibitor is a gamma-secretase inhibitor.

6. The method of claim 5, wherein said gamma-secretase inhibitor is (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide.

7. The method according to claim 4, wherein the NOTCH1 specific inhibitor is a gamma-secretase inhibitor.

8. The method according to claim 7, wherein the gamma-secretase inhibitor is (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide.

9. The method according to claim 4, wherein the MYB specific inhibitor is administered in combination with the NOTCH1 specific inhibitor.

10. The method according to claim 9, wherein the MYB specific inhibitor is a MYB specific siRNA and the NOTCH1 specific inhibitor is a gamma-secretase inhibitor.

11. The method according to claim 10, wherein the gamma-secretase inhibitor is (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide.

12. The method according to claim 1, wherein determining the presence of a duplication of the MYB gene in the T-cell acute lymphoblastic leukemia cell comprises determining the presence of at least three copies of the MYB gene.

* * * * *